United States Patent [19]
Letton et al.

[11] Patent Number: 6,151,958
[45] Date of Patent: *Nov. 28, 2000

[54] ULTRASONIC FRACTION AND FLOW RATE APPARATUS AND METHOD

[75] Inventors: Winsor Letton, Houston, Tex.; Klaus Zanker, Larbert, United Kingdom

[73] Assignee: Daniel Industries, Inc., Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/613,478

[22] Filed: Mar. 11, 1996

[51] Int. Cl.$^7$ .......................... G01N 29/02; G01N 29/16; G01N 29/18; G01N 29/20
[52] U.S. Cl. .................. 73/61.79; 73/24.01; 73/24.04
[58] Field of Search .................. 73/19.03, 19.04, 73/24.01, 24.04, 29.01, 61.45, 61.44, 61.79, 865.5

[56] References Cited

U.S. PATENT DOCUMENTS

| | | | |
|---|---|---|---|
| H000608 | 3/1989 | Goolsby | 73/861.25 |
| 3,623,363 | 11/1971 | Dory | 73/61.45 X |
| 4,080,837 | 3/1978 | Alexander et al. | 73/61.45 |
| 4,138,879 | 2/1979 | Liebermann | 73/19.03 |
| 4,763,525 | 8/1988 | Cobb | 73/24.01 X |
| 5,325,703 | 7/1994 | Magori | 73/24.04 |
| 5,415,048 | 5/1995 | Diatschenko et al. | 73/861.04 |
| 5,537,854 | 7/1996 | Phillips et al. | 73/24.01 |
| 5,714,691 | 2/1998 | Hill . | |
| 5,719,329 | 2/1998 | Jepson | 73/861.04 |
| 5,792,962 | 8/1998 | Constant et al. | 73/831.04 |

FOREIGN PATENT DOCUMENTS

| | | | |
|---|---|---|---|
| 691527 | 10/1996 | European Pat. Off. . | |
| 838552 | 6/1981 | U.S.S.R. | 73/19.03 |
| 14382 | 7/1993 | WIPO . | |

Primary Examiner—Daniel S. Larkin
Attorney, Agent, or Firm—Conley, Rose & Tayon

[57] ABSTRACT

Disclosed is a method for measuring the amount of liquid in a volume of gas and the associated flow rates. A method of determining the percentage of a liquid present in a volume of gas is provided. The method comprises the steps of impressing the volume of gas with ultrasonic energy, receiving the ultrasonic energy impressed upon and traversing the volume of gas, measuring the received ultrasonic energy which has traversed the volume of gas, evaluating various parameters of the measured ultrasonic energy for variations which variations are a function of the liquid fraction in the volume of gas. A method is provided for determining the flow rates associated with a liquid-gas mixture.

22 Claims, 9 Drawing Sheets

---

IMPRESSING THE VOLUME OF GAS WITH ULTRASONIC ENERGY

↓

RECEIVING THE ULTRASONIC ENERGY IMPRESSED UPON AND TRAVERSED THROUGH THE VOLUME OF GAS

↓

MEASURING THE RECEIVED ULTRASONIC ENERGY WHICH HAS TRAVERSED THE VOLUME OF GAS

↓

EVALUATING VARIOUS PARAMETERS OF THE MEASURED ULTRASONIC ENERGY FOR VARIATIONS WHICH VARIATIONS ARE A FUNCTION OF THE LIQUID FRACTION IN THE VOLUME OF GAS

ULTRASONIC FRACTION AND FLOW RATE APPARATUS AND METHOD

FIELD OF THE INVENTION

The present invention relates generally to an apparatus and a method for measuring the fraction of a component of a mixture and the associated flow rate. More particularly, the present invention relates to an ultrasound apparatus and a method for determining the percentage of liquid in a volume of gas flowing through a conduit, and the associated flow rates.

BACKGROUND OF THE INVENTION

The ability to measure the amount of liquid in a volume of gas is extremely important. Numerous occasions require the accurate measurement of the amount of liquid in a gas. Such accuracy is extremely important to buyers and sellers of natural gas. If the gas contains water, a buyer does not want to pay for the gas on the basis of the gross volume shipped to him. Rather, he wants to pay only for the net amount of gas present in the total volume delivered. On the other hand, if the gas contains "natural gas liquids" or condensates, the seller wants to be compensated for this energy-rich liquid. In both cases, it is very important to know the gas and liquid fractions. Net gas measurement is also required in production fields.

There are a number of instruments which have been used to make various types of measurements. Techniques are available to measure the properties of a mixture. For example, the conductivity of the mixture may be measured at a relevant frequency.

Radiation is grouped into three general categories: electromagnetic, mechanical, and particle radiation. Mechanical radiation requires a material medium to propagate energy from one place to another. For example, sound, produced by vibration, cannot travel through a vacuum, but does travel freely through gases, liquids, or solids. Since mechanical radiation is primarily produced by vibration, detectors of this kind of radiation are typically things that vibrate, such as the diaphragm in a microphone, telephone, or transducer. Mechanical radiation in the form of ultrasound is a valuable tool in measurement technology.

For the purpose of the present invention, generally, sounds above approximately 20,000 hertz are defined as ultrasound. Ultrasound has been used to identify flaws in industrial parts, to diagnose and treat diseases, and to explore the ocean's depths. Ultrasonic waves can be generated by mechanical, electromagnetic, and thermal devices with frequencies ranging from 20,000 to several billion hertz.

The field of ultrasonics involves producing vibrational waves of above 20,000 hertz in solids, liquids, gases, and other elastic materials. High-power applications include ultrasonic welding and drilling. Ultrasonic waves are frequently used to detect internal defects in solid materials. For example, railroads use ultrasonic waves to locate cracks within railroad tracks. With particular emphasis to the present invention, ultrasonics are used in flow metering technology.

It is appreciated that the present invention is applicable for solids, liquids, gases, and other elastic materials. As used for the present invention, the terms liquid and condensate are used interchangeably. It is appreciated by those skilled in the art that all condensates are liquids, but all liquids are not condensates. For example, in the natural gas industry, a condensate is a hydrocarbon. More particularly, a condensate could be considered a liquid hydrocarbon lighter than fuel oil. Alternately, water is a liquid but not a condensate.

It is a feature of the present invention to provide an apparatus and method for determining the percentage of a liquid or condensate in a volume of gas flowing through a conduit and the associated flow rates.

Yet another feature of the present invention is to provide an apparatus and method for determining the percentage of liquid or condensate in a volume of gas where the amount of condensate present is in the range from 0 to 100 percent.

Yet another feature of the present invention is to provide an apparatus and method for determining the flow rate of liquid or condensate in a volume of gas where the amount of condensate present is in the range from 0 to 100 percent.

Still a further feature of the present invention is to provide a method and apparatus for determining the liquid or condensate content in a volume of gas and its associated flow rate by measurement of the volume's ultrasonic properties.

It is a further feature of the present invention to provide an apparatus and method for determining the percentages of gas, liquid or condensate in an gas, liquid, condensate mixture by measuring its ultrasonic properties.

Briefly stated, the foregoing and numerous other features, objects and advantages of the present invention will become readily apparent upon reading the detailed description, claims and drawings set forth hereinafter. Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, an ultrasound apparatus and a method for determining the percentage of liquid in a volume of gas flowing through a conduit is provided. Particularly, a method of determining the percentage of a fluid present in a volume of gas is provided. The method comprises the steps of impressing the volume of gas with ultrasonic energy, receiving the ultrasonic energy impressed upon and traversing the volume of gas, measuring the received ultrasonic energy which has traversed the volume of gas, evaluating various parameters of the measured ultrasonic energy for variations which variations are a function of the liquid fraction in the volume of gas.

More particularly, the step of impressing the volume of gas with ultrasonic energy includes transmitting vibrations through the volume of gas. The step of transmitting vibrations through the volume of gas comprises transmitting acoustic frequencies above approximately 20,000 hertz through the volume of gas. The step of measuring the received ultrasonic energy which has traversed the volume of gas provides for transducing the signal for generating an electronic signal. Still more particularly, the step of evaluating various parameters of the measured ultrasonic energy for variations provides for evaluating the gain associated with the measured signal for variations. The variations associated with the measure of attenuation of the ultrasonic signal or the gain of the instrument are a function of the liquid fraction in the volume of gas. The step of evaluating various parameters of the measured ultrasonic energy for variations includes evaluating the transit time (t) of a signal for variations which variations are a function of the liquid fraction in the volume of gas. Similarly, the step of evaluating various parameters of the measured ultrasonic energy for variations includes evaluating the standard deviation of the transit time ($\sigma t$) of a single signal for variations which variations are a function of the liquid fraction in the volume of gas. Further, the step of evaluating various parameters of the measured ultrasonic energy for variations includes evaluating the travel time difference ($t_2-t_1$) associated with the measured signal for variations which variations are a function of the liquid fraction in the volume of gas. Still further, the step of evaluating various parameters of the measured ultrasonic energy for variations can also include evaluating the standard deviation of the travel time difference ($\sigma(t_2-t_1)=\sigma(\Delta t)$) associated with the measured signal for variations which variations are a function of the liquid fraction in the volume of gas. Further, evaluating various parameters of the measured ultrasonic energy for variations includes evaluating the sound velocity characteristics associated with variations of the measured signal which variations are a function of the liquid fraction in the volume of gas.

Still further, the method provides for evaluating any stratified flow characteristics associated with the liquid fraction in the volume of gas such that the stratified flow characteristics are a function of the liquid fraction in the volume of gas. Similarly, the method provides for evaluating any mist flow characteristics associated with the liquid fraction in the volume of gas such that the mist flow characteristics are a function of the liquid fraction in the volume of gas. The method of the present invention can determine which characteristics are appropriate for a particular situation.

The method of the present invention of determining the percentage of a liquid present in a volume of gas is especially adaptable for use with natural gas. The variations of the parameters of the measured ultrasonic energy are a function of the liquid fraction in the volume of gas and provide a function applicable over a range of liquid fractions.

Still further, the present invention provides an apparatus for determining the percentage of a liquid present in a volume of gas. The apparatus comprises a device for impressing the volume of gas with ultrasonic energy, a detector for receiving ultrasonic energy which has traversed the volume of gas, and a processor for evaluating various parameters of the measured ultrasonic energy for variations which variations are a function of the liquid fraction in the volume of gas. For example, particular variations of the measured signal correspond to, and are a function of, particular changes in properties, for example, the relative signal amplitude is a measure of the attenuation of the ultrasonic signal. The apparatus of the present invention can employ a typical ultrasonic flow meter. The apparatus has a processor for evaluating the mist flow characteristics or the stratified flow characteristics associated with the liquid fraction in the volume of gas. The mist flow characteristics and the stratified flow characteristics are a function of the liquid fraction in the volume of gas.

Still further, a method is provided for determining the flow rates associated with a liquid-gas mixture. The liquid-gas mixture has a liquid component and a gas component. The method comprises the steps of impressing the mixture with ultrasonic energy, measuring the ultrasonic energy which has traversed the mixture, evaluating various parameters of the measured ultrasonic energy for variations which variations are a function of the components of the mixture, determining the respective velocities, and determining the associated flow rates.

Also provided is an apparatus for determining the flow rates associated with a liquid-gas mixture having a liquid component and a gas component. The apparatus comprises a device for impressing the volume of gas with ultrasonic energy, a detector for measuring ultrasonic energy which has traversed the volume of gas, and a processor for evaluating various parameters of the measured ultrasonic energy for variations which variations are a function of the liquid fraction in the volume of gas, a device for determining the respective velocities, and a device for determining the associated flow rates.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

Figure 1:
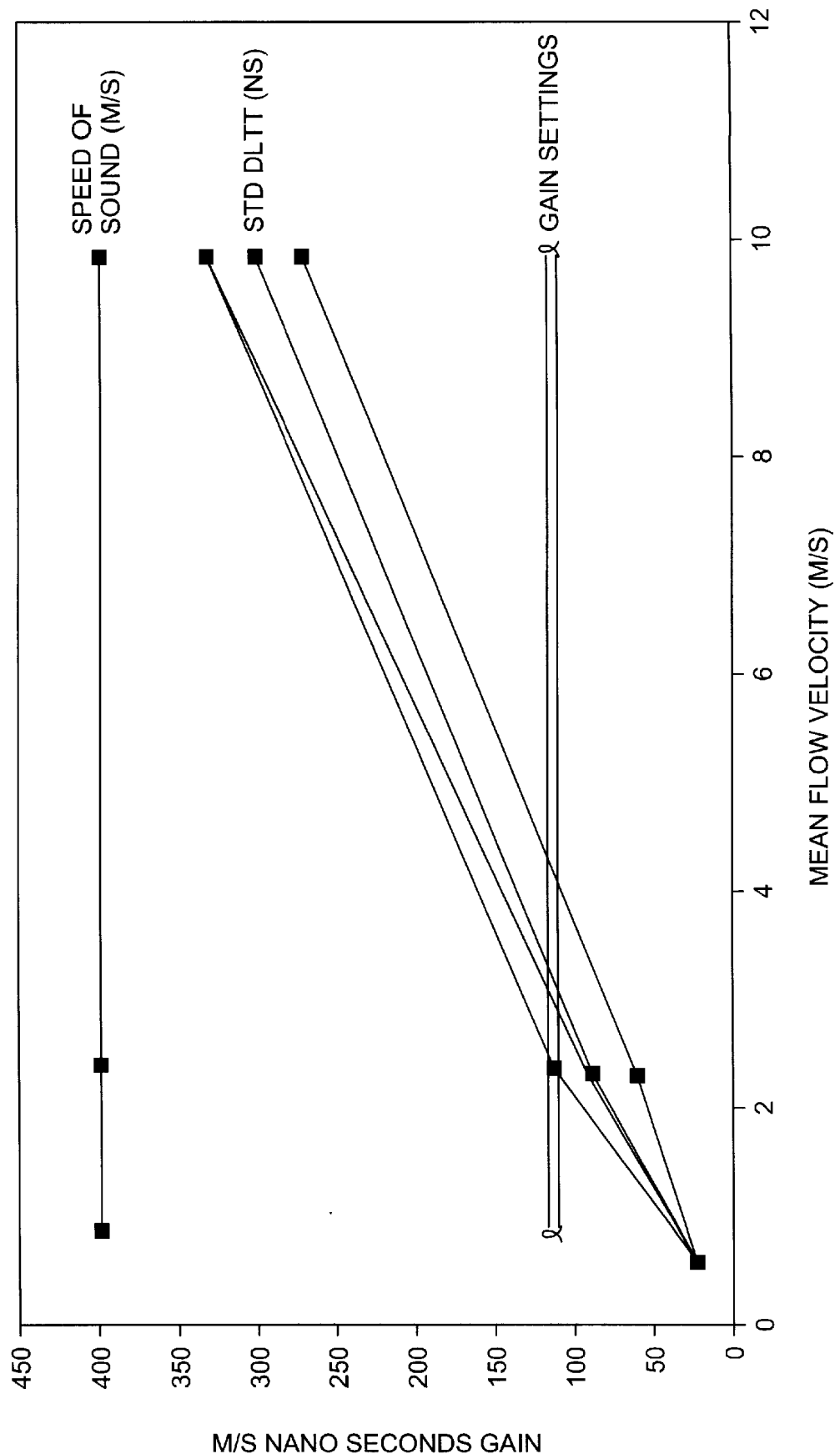
FIG. 1 is a graph of the mean flow velocity versus the gain, the speed of sound and the standard deviation of the travel time difference of the ultrasonic flowmeter for normal liquid-free service.

FIG. 1 is a graph of the mean flow velocity versus the gain, the speed of sound and the standard deviation of the travel time difference of the ultrasonic flowmeter for normal liquid-free service. FIG. 1 illustrates that a volume of gas which is free of moisture. The attenuation/gain characteristic and the speed of sound are constant. However, the standard deviation of the travel time difference ($\sigma(\Delta t)$) varies. FIG. 1 illustrates a base condition. Particularly as shown in FIG. 1, the speed of sound is unaffected by the flow velocity. Also in FIG. 1, the amplifier gains associated with the equipment are unaffected by flow velocity when no liquid is present in the volume of gas. The standard deviation of the travel time difference ($\Delta t$) is affected by flow velocity, in roughly the magnitudes shown, for a 150-mm meter.

Figure 2:
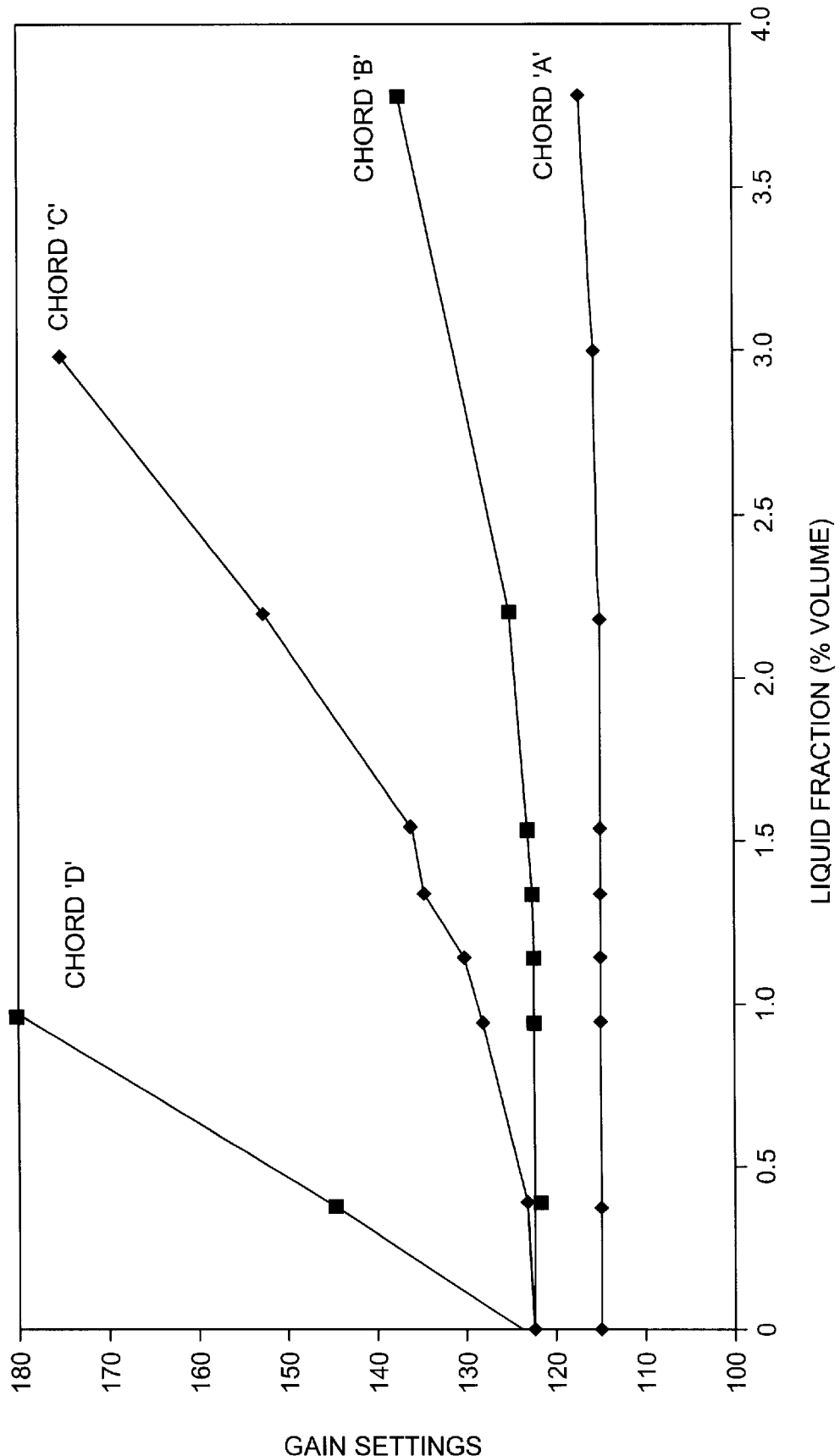
FIG. 2 is a graph of the liquid fraction versus the gain of the ultrasonic flowmeter.

FIG. 2 is a graph of the liquid fraction versus the gain of the ultrasonic flow meter. In a typical ultrasonic flow meter, the signal gain is controlled. The meter electronics attempts to maintain signals at a constant amplitude so that digitization is readily accomplished. Thus, if for whatever reason the signal is attenuated, the amplifier gain of the receiver is boosted to overcome the attenuation. Typically, the transmitted signal power will remain constant. However, the amplifier gain associated with the receiver is a measure of attenuation.

FIG. 2 illustrates that the attenuation along chord D is greater than any other chord. The attenuation along chord C illustrates the next highest attenuation, and the attenuation along chord B is yet still lower, as is the attenuation along chord A. The meter used to acquire the data illustrated in FIG. 2 was horizontally arranged such that chord D was at the bottom of the meter, chord C was slightly above chord D, chord B was slightly above chord C, and chord A was above chord B. The data of FIG. 2 is readily explainable to gravitational effects. Gravity keeps the misting of the condensate dense around the bottom of the meter, i.e., in the vicinity of chords D and C. The mixture traveling along the top of the associated meter is significantly less dense as illustrated by the data associated with chords A and B.

Figure 3:
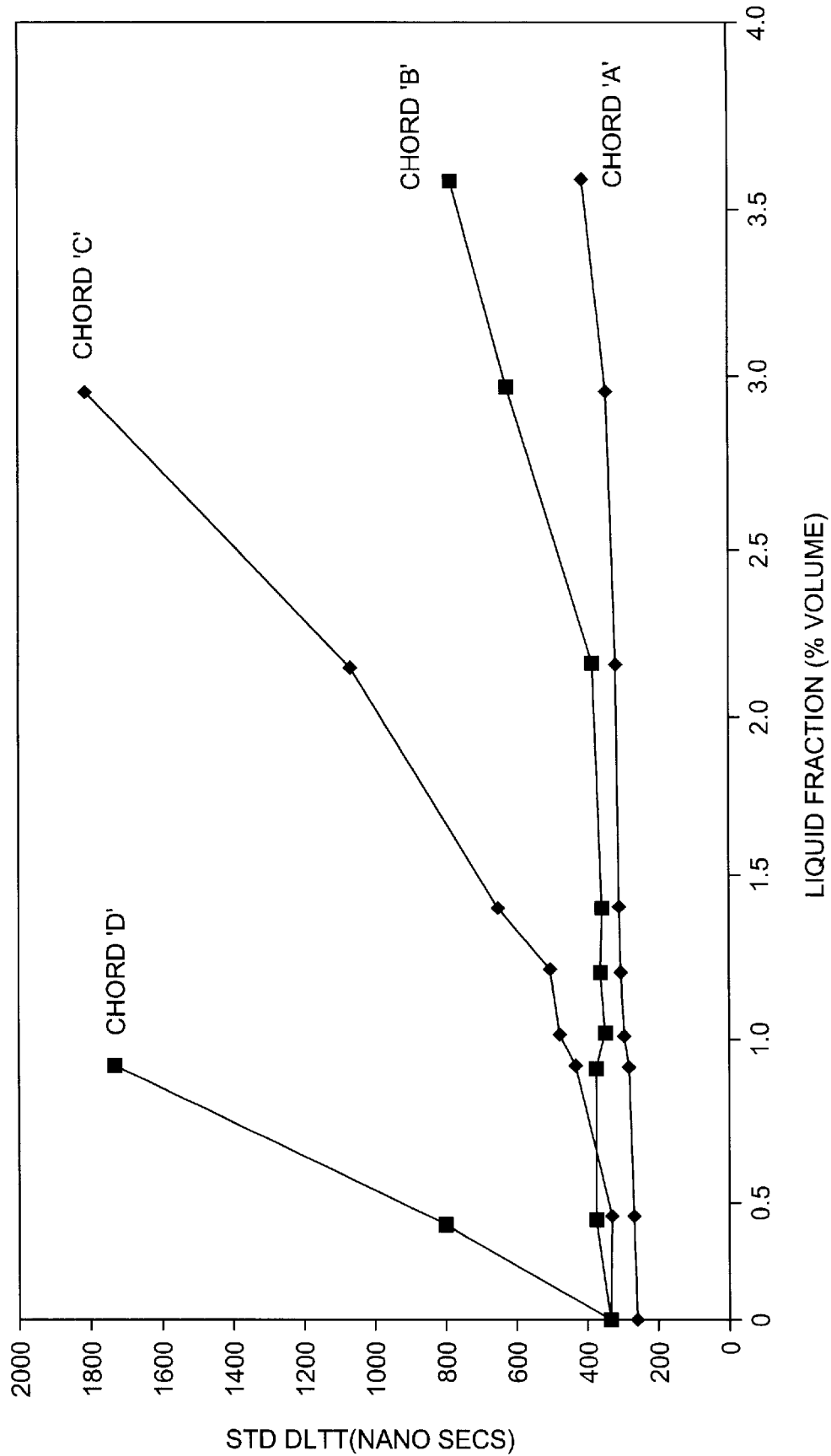
FIG. 3 is a graph of the liquid fraction versus the standard deviation of the travel time difference ($\Delta t$) of the ultrasonic flowmeter.

FIG. 3 is a graph of the liquid fraction versus the deviation of the travel time difference of the ultrasonic flow meter. The standard deviation of the travel time difference ($\Delta t$) measurements associated with FIG. 3 is caused by increased liquid fraction. As with FIG. 2, the data in FIG. 3 illustrates that the effect is greatest at the bottom of the meter, near chords C and D, and less at the top of the meter, near chords A and B. It should be noted that the high liquid fraction increases the standard deviation from approximately 300 nanoseconds in dry gas to approximately 1800 nanoseconds with respect to chords D and C with liquid.

Figure 5:
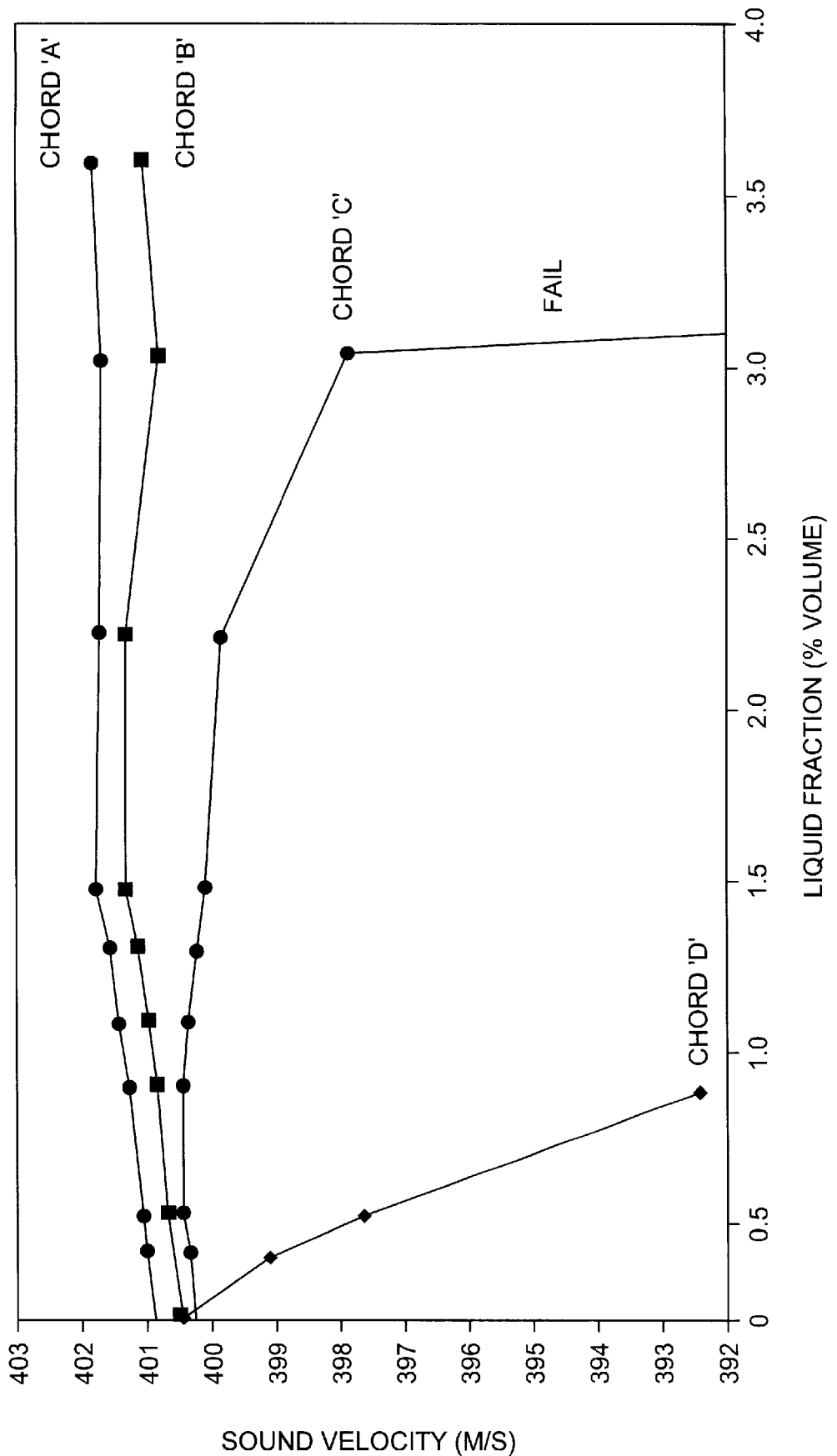
FIG. 5 is a graph of the liquid fraction versus the sound velocity associated with the ultrasonic flowmeter for a gas velocity of 10 meters per second.

Those skilled in the art appreciate that the gradients of the respective measurements can be used as well as the direct measurements. For example, FIGS. 2, 3, and 5 illustrate the gradients between chords. The gradients between chords are readily available for use as data in practicing the present invention. Thus, a gradient between chords can be used. Also, a difference between gradients can be used. Further, the standard deviation of a gradient between chords can be used. Similarly, the standard deviation of the difference between gradients between chords can be used. As can be appreciated, other parameters can be adapted for use in practicing the present invention.

Figure 4:
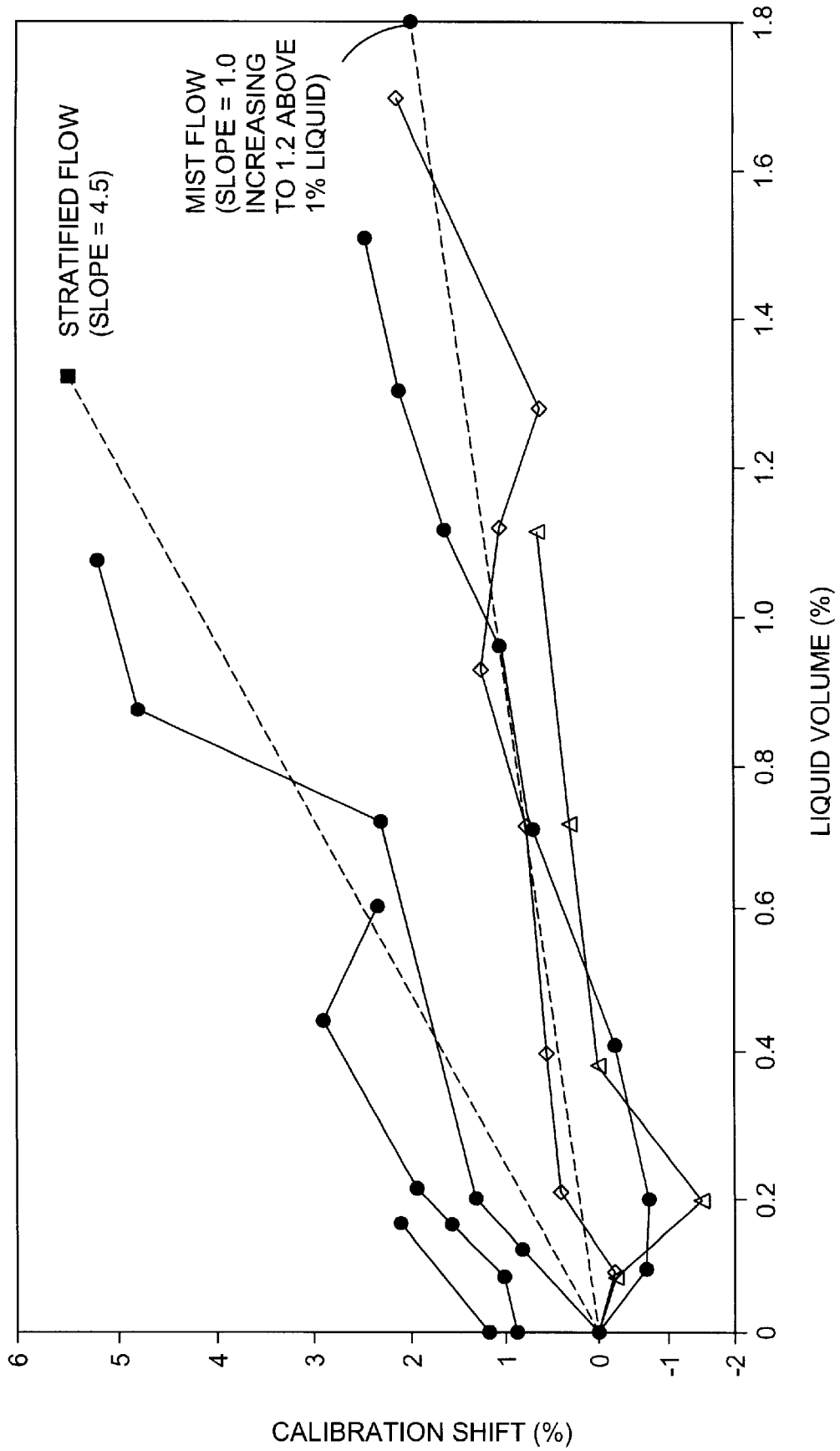
FIG. 4 is a graph of the liquid volume versus the calibration shift of the ultrasonic flowmeter.

FIG. 4 is a graph of the liquid volume versus the calibration shift of the ultrasonic flow meter. The calibration shift is also termed the meter over-reading. The calibration shift is provided as a function of the liquid volume for various flow rates in FIG. 4. The data provided a marked distinction between stratified flow and mist flow. For stratified flow, the liquid hold up of the stratified flow causes a significant gas measurement error. It has been determined that the gas measurement error associated with the stratified flow situation is about 4.5% for every 1% of liquid volume. For the mist flow situation, the mist droplets are carried at the same flow rate as the gas. Thus, the calibration shift is approximately 1% for each 1% of liquid volume.

FIG. 5 is a graph of the liquid fraction versus the sound velocity associated with the ultrasonic flow meter of the present invention. FIG. 5 illustrates the sound velocity measured on each chord at a flow velocity of 10 meters per second. Chords A and B are essentially unaffected at these levels. However, chords C and D show a definite dependence on the relative liquid content in the volume of gas. It should be noted that the maximum change of the velocity of sound was approximately 8 meters per second, or 2%.

Figure 6:
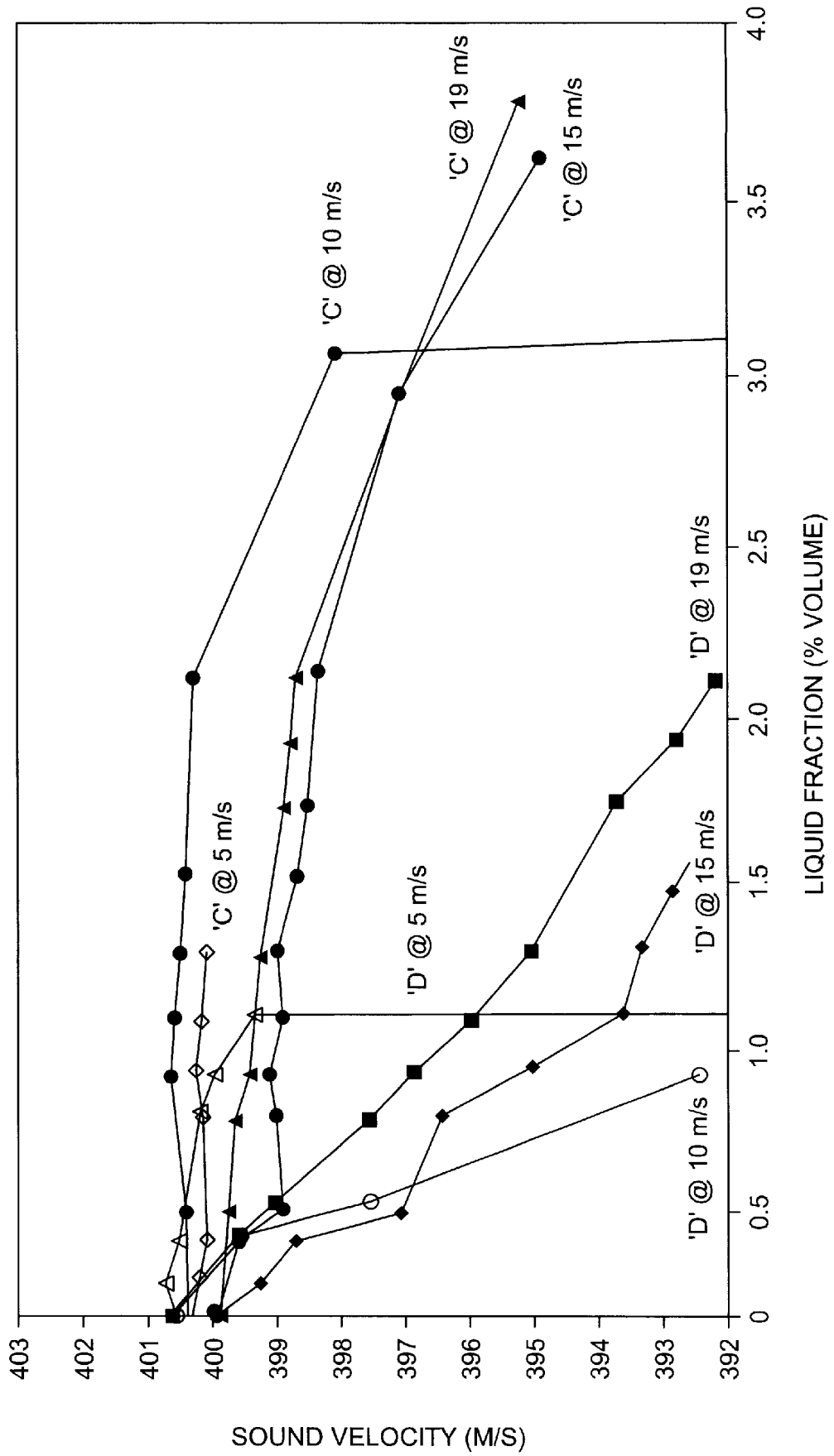
FIG. 6 is a graph of the liquid fraction versus the sound velocity associated with the ultrasonic flowmeter for several gas velocities.
Figure 7:
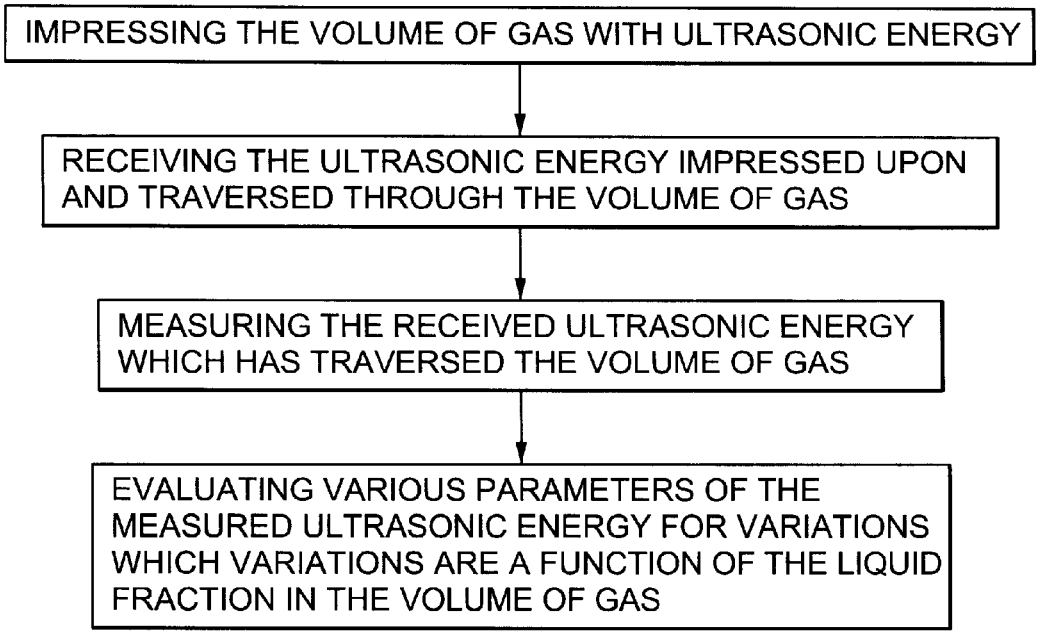
FIG. 7 is a flow chart illustrating one embodiment of the method of determining the liquid fraction in a volume of gas as practiced by the present invention.

FIG. 6 is a graph of the liquid fraction versus the sound velocity associated with the ultrasonic flow meter of the present invention. In FIG. 6, the velocity of sound for chord C and D is plotted for various flow velocities. A comparison of the curves measured at approximately 5 meters per second and those of higher flows is important. It is anticipated that the flow crosses from a stratified situation to a mist flow situation somewhere between 5 and 10 meters per second.

Thus, the present invention provides for the discovery that various parameters of a measured ultrasonic signal transmitted through a volume of gas has certain variations which are a function of the liquid fraction in the gas. Particularly, a method can be provided whereby the percentage of a liquid present in a volume of gas can be determined. The method comprises the steps of impressing the volume of gas with ultrasonic energy, receiving the ultrasonic energy impressed upon and traversed through the volume of gas, measuring the received ultrasonic energy which has traversed the volume of gas, and evaluating various parameters of the measured ultrasonic energy for variations which are a function of the liquid fraction in the volume of gas.

Figure 8:
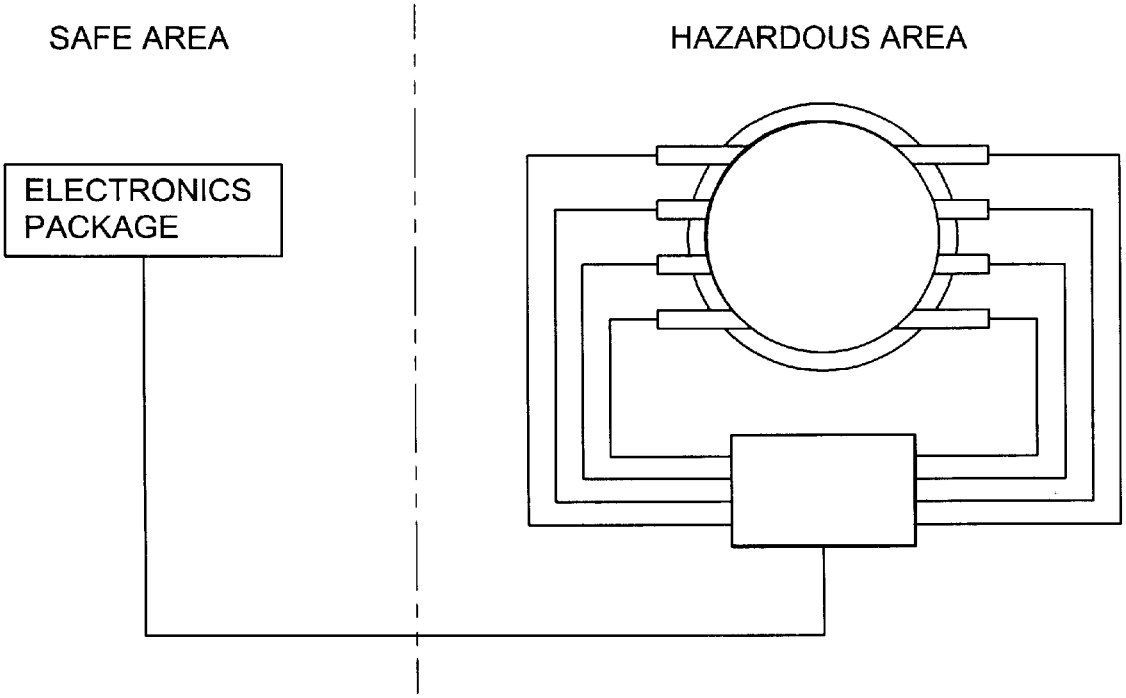
FIG. 8 is an overview illustration of an apparatus employing the present invention.

FIG. 8 is a general illustration of a representative apparatus for employing the present invention.

Figure 9:
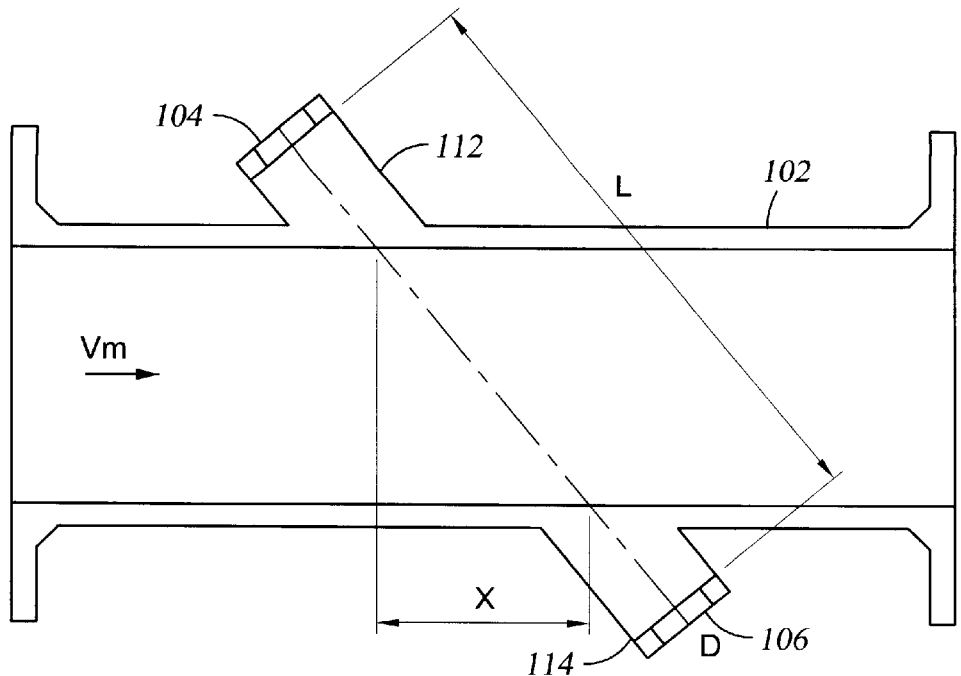
FIG. 9 is a perspective cross-section of a pipe illustrating one embodiment of the orientation of transducers which could be used in association with the present invention.

FIG. 9 is a perspective cross-section of a pipe illustrating one embodiment of the orientation of transducers which could be used in practicing the present invention. The pipe 102 is adapted for receiving the transducers 104, 106. The transducers 104, 106 are displaced on opposite sides of the pipe 102 by a distance L between each transducer. The transducers 104, 106 are longitudinally displaced by a distance of X. The pipe 102 has ports 112, 114 for receiving the transducers 104, 106, respectively.

Figure 10:
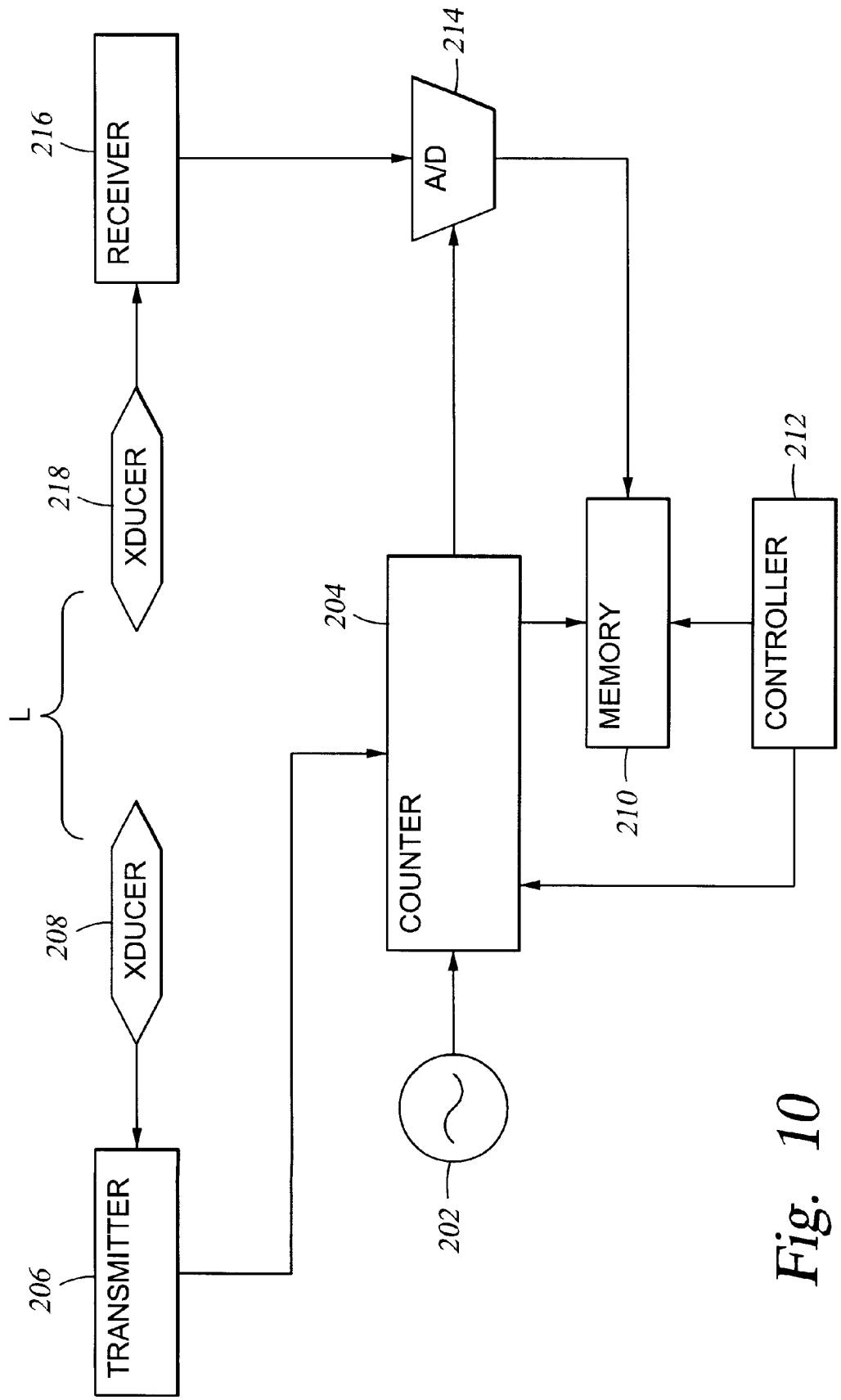
FIG. 10 is a diagram illustrating electronics associated with the apparatus of the present invention.

FIG. 10 is a block diagram illustrating the apparatus 200 of the present invention. The apparatus 200 of the present invention comprises a clock 202, a counter 204, a transmitter 206, a first transducer 208, a memory 210, a controller 212, an analog-to-digital converter 214, a receiver 216, and a second transducer 218. The clock 202 is used for timing.

In operation, the transmitter 206 is fired. The apparatus 200 starts digitizing. The A/D converter 214 is activated. The counter 204 starts counting. At every count of the counter 204, the A/D converter 214 places a magnitude from the receiver 216 into the next location in the memory 210. Thus, as time passes, the memory 210 may develop curves as illustrated in FIGS. 2, 3, and 5. It is appreciated by those skilled in the art that all available phenomena are typically evaluated. Evaluating all relevant phenomena, including without limitation data illustrated in FIGS. 2, 3, and 5, provides a level of confidence in the date. The data accumulated in the memory 210 is processed as previously discussed to determine the time measurement.

Although the apparatus 200 illustrated in FIG. 10 indicates there are dual transducers 208, 218, it can be appreciated that a single transducer may be readily adapted for practicing the present invention. For example, a single transceiver device may be used to measure an attenuated signal. Further, it can be appreciated by those skilled in the art that various system arrangements are readily available for practicing the present invention. Additional circuitry can be used to alternate the transmitter 206 and the receiver 218. Also, techniques or equipment can be readily adapted by those skilled in the art to delay the start of the A/D converter 214 until a later time prior to the arrival of the signal.

In practicing the present invention, the same device can be used to determine the flow rate and the fractions. The present invention can also be practiced by using the present fraction meter in association with another type of flow rate meter, i.e., not an ultrasonic meter. Further, the orientation of the meter is independent with respect to practicing the present invention. The meter could be oriented horizontally, vertically or at an intermediate orientation.

Particularly, a method of determining the percentage of a fluid present in a volume of gas is provided. The method comprises the steps of impressing the volume of gas with ultrasonic energy, receiving the ultrasonic energy impressed upon and traversing the volume of gas, measuring the received ultrasonic energy which has traversed the volume of gas, evaluating various parameters of the measured ultrasonic energy for variations which variations are a function of the liquid fraction in the volume of gas.

More particularly, the step of impressing the volume of gas with ultrasonic energy includes transmitting vibrations through the volume of gas. The step of transmitting vibrations through the volume of gas comprises ultrasonic frequencies through the volume of gas. The step of measuring the received ultrasonic energy which has traversed the volume of gas provides for transducing the signal for generating an electronic signal. Still more particularly, the step of evaluating various parameters of the measured ultrasonic energy for variations provides for evaluating the gain associated with the measured signal for variations. The variations associated with the gain are a function of the liquid fraction in the volume of gas. Also, the step of evaluating various parameters of the measured ultrasonic energy for variations includes evaluating the standard deviation of the travel time difference associated with the measured signal for variations which variations are a function of the liquid fraction in the volume of gas.

Still further, the method provides for evaluating any stratified flow characteristics associated with the liquid fraction in the volume of gas such that the stratified flow characteristics are a function of the liquid fraction in the volume of gas. Similarly, the method provides for evaluating any mist flow characteristics associated with the liquid fraction in the volume of gas such that the mist flow characteristics are a function of the liquid fraction in the volume of gas. The method of the present invention can determine which characteristics are appropriate for a particular situation.

The method of the present invention of determining the percentage of a fluid present in a volume of gas is especially adaptable for use with natural gas. The variations of the parameters of the measured ultrasonic energy are a function of the liquid fraction in the volume of gas and provide a function applicable over a range of liquid fractions.

Still further, the present invention provides an apparatus for determining the percentage of a fluid present in a volume of gas. The apparatus comprises a device for impressing the volume of gas with ultrasonic energy, a detector for receiving ultrasonic energy which has traversed the volume of gas, and a processor for evaluating various parameters of the measured ultrasonic energy for variations which variations are a function of the liquid fraction in the volume of gas. For example, particular variations of the measured signal correspond to, and are a function of, particular changes in the gain associated with the measured signal. The apparatus of the present invention can employ a typical ultrasonic flow meter. The apparatus has a processor for evaluating the mist flow characteristics or the stratified flow characteristics associated with the liquid fraction in the volume of gas as well as the gas velocity. The mist flow characteristics and the stratified flow characteristics are a function of the liquid fraction in the volume of gas.

Figure 11:
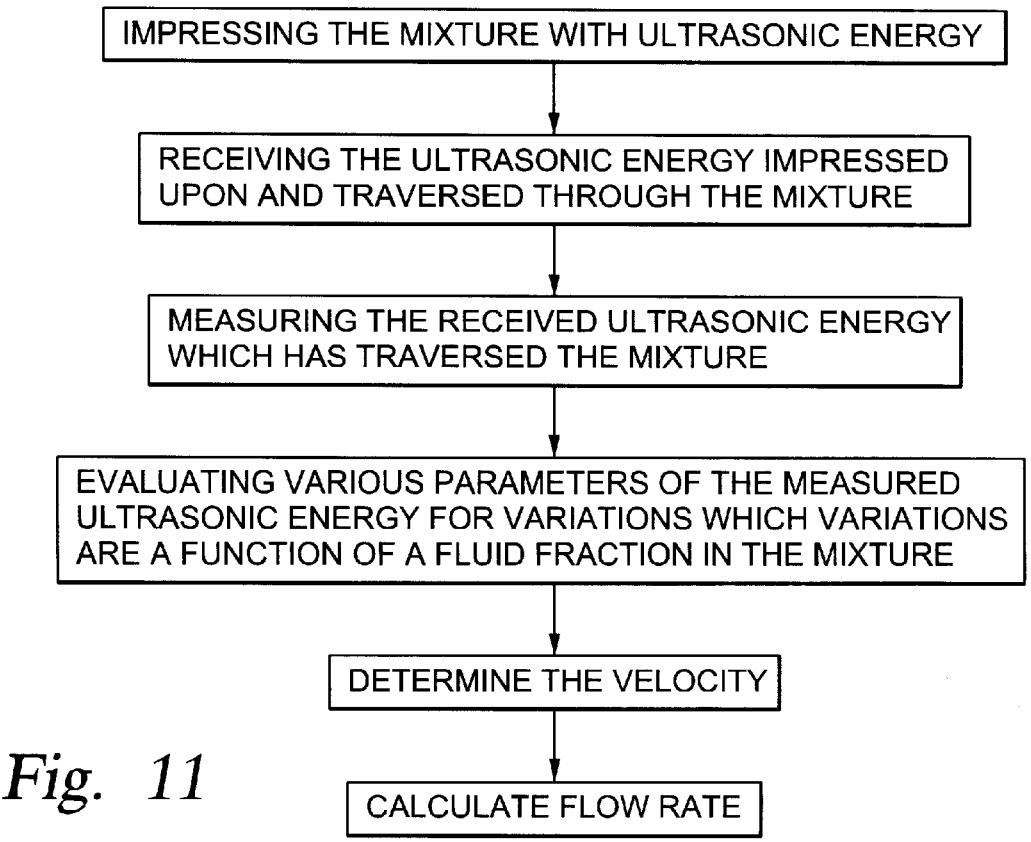
FIG. 11 is a flow chart illustrating one embodiment of the method of determining the flow rate associated with the liquid fraction in a volume of gas as well as the gas as practiced by the present invention.

In yet another embodiment of the present invention, a flow rate meter and method is provided. FIG. 11 illustrates the embodiment of the present invention wherein the gas and liquid flow rates are calculated. FIG. 11 is descriptive of a mixture having a gas fraction and a liquid fraction, both fractions termed fluid. The mixture is impressed with ultrasonic energy. The received ultrasonic energy is received and measured. Various parameters of the measured ultrasonic energy are evaluated for variations. The variations are a function of a fluid fraction in the mixture. The velocity is determined. Using the velocity and the fluid fraction, a flow rate is calculated. It is appreciated by those skilled in the art that the calculated flow rate can be for the gas fraction or the liquid fraction, or both. Typically, the embodiment illustrated in FIG. 11 determines the velocity of the signals counter propagating in nature to get the velocity. The velocity of the ultrasonic signal between transducers is used to compute the flow rate. More particularly, the present invention provides for the measurement of the flow velocity of a fluid in a pipe comprising two or more transducers mounted on either side of the pipe and directed obliquely in relation to the direction of the flow, which transducers transmit and/or receive sonic pulses to and from each other.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A method of determining the percentage of a liquid present in a volume of gas, the method comprising:
   (a) impressing the volume of gas with ultrasonic energy:
   (b) measuring the ultrasonic energy which has traversed the volume of gas; and
   (c) evaluating at least one parameter of the measured ultrasonic energy for variations, which variations are a function of the liquid fraction in the volume of gas; and
   (d) determining said percentage of said liquid present in said volume of gas based upon said at least one parameter.

2. A method of determining the percentage of a liquid present in a volume of gas as defined in claim 1 wherein impressing the volume of gas with ultrasonic energy comprises transmitting vibrations through the volume of gas.

3. A method of determining the percentage of a liquid present in a volume of gas as defined in claim 2 wherein transmitting vibrations through the volume of gas comprises transmitting acoustic frequencies above approximately 20,000 hertz.

4. A method of determining the percentage of a liquid present in a volume of gas as defined in claim 1 wherein measuring the ultrasonic energy which has traversed the volume of gas comprises transducing the signal for generating an electronic signal.

5. A method of determining the percentage of a liquid present in a volume of gas as defined in claim 1 wherein impressing the volume of gas with ultrasonic energy includes transmitting at least two ultrasonic waves through said volume of gas, all of said ultrasonic waves being of approximately the same energy, and further wherein at least one parameters of the measured ultrasonic energy for variations evaluating comprises evaluating the gain of instrumentation associated with the measured signal for variations, which variations are a function of the liquid fraction in the volume of gas.

6. A method of determining the percentage of a liquid present in a volume of gas as defined in claim 1 wherein evaluating at least one parameter of the measured ultrasonic energy for variations comprises evaluating the attenuation of the ultrasonic energy which has traversed the volume of gas for variations, which variations are a function of the liquid fraction in the volume of gas.

7. A method of determining the percentage of a liquid present in a volume of gas as defined in claim 1 wherein evaluating at least one parameter of the measured ultrasonic energy for variations comprises evaluating the standard deviation of the travel time difference associated with the measured signal for variations, which variations are a function of the liquid fraction in the volume of gas.

8. A method of determining the percentage of a liquid present in a volume of gas as defined in claim 1 wherein evaluating at least one parameter of the measured ultrasonic energy for variations comprises evaluating the standard deviation of the travel time associated with the measured signal for variations, which variations are a function of the liquid fraction in the volume of gas.

9. A method of determining the percentage of a liquid present in a volume of gas as defined in claim 1 wherein evaluating at least one parameter of the measured ultrasonic energy for variations comprises evaluating the velocity of sound associated with the measured signal for variations, which variations are a function of the liquid fraction in the volume of gas.

10. A method of determining the percentage of a liquid present in a volume of gas as defined in claim 1 wherein evaluating at least one parameter of the measured ultrasonic energy for variations comprises evaluating any stratified flow characteristics associated with the liquid fraction in the volume of gas, such that the stratified flow characteristics are a function of the liquid fraction in the volume of gas.

11. A method of determining the percentage of a liquid present in a volume of gas as defined in claim 1 wherein evaluating at least one parameter of the measured ultrasonic energy for variations comprises evaluating any mist flow characteristics associated with the liquid fraction in the volume of gas, such that the mist flow characteristics are a function of the liquid fraction in the volume of gas.

12. A method of determining the percentage of a liquid present in a volume of gas as defined in claim 1 wherein evaluating at least one parameter of the measured ultrasonic energy for variations comprises evaluating at least one of mist flow characteristics and stratified flow characteristics associated with the liquid fraction in the volume of gas, such that the characteristics are a function of the liquid fraction in the volume of gas.

13. A method of determining the percentage of a liquid present in a volume of gas as defined in claim 12 wherein evaluating at least one of mist flow characteristics and stratified flow characteristics associated with the liquid fraction in the volume of gas, such that the characteristics are a function of the liquid fraction in the volume of gas comprises determining which characteristics are appropriate for the particular situation.

14. A method of determining the percentage of a liquid present in a volume of gas as defined in claim 1 wherein impressing the volume of gas with ultrasonic energy comprises impressing natural gas with ultrasonic energy.

15. A method of determining the percentage of a liquid present in a volume of gas as defined in claim 1 wherein impressing the volume of gas with ultrasonic energy comprises impressing a hydrocarbon fluid with ultrasonic energy.

16. A method of determining the percentage of a liquid present in a volume of gas as defined in claim 1 wherein evaluating various parameters of the measured ultrasonic energy for variations, which variations are a function of the liquid fraction in the volume of gas, comprises evaluating the function over a range of liquid fractions.

17. A method of determining the percentage of a liquid present in a volume of gas as defined in claim 16 wherein evaluating the function of variations of measured ultrasonic energy over a range of liquid fractions comprises determining a specific liquid fraction defined by the variations of the measured ultrasonic energy.

18. A method as defined in claim 1 further comprising of determining the velocity and determining the flow rates.

19. The method of claim 1, wherein said at least one parameter is two or more parameters.

20. The method of claim 1, wherein said impressing of said volume of gas with ultrasonic energy is provided over two or more chords.

21. The method of claim 1, wherein said evaluating and said determining are based upon said at least one parameter measured from at least two chords.

22. A method of determining the percentage of a liquid present in a volume of gas, the method comprising the steps of:

(a) a step for impressing the volume of gas with ultrasonic energy;

(b) a step for measuring the ultrasonic energy which has traversed the volume of gas;

(c) a step for evaluating at least one parameter of the measured ultrasonic energy for variations, which variations are a function of the liquid fraction in the volume of gas; and (d) a step for determining said percentage of said liquid present in said volume of gas based upon said at least one parameter.

* * * * *